United States Patent
Bauch et al.

(10) Patent No.: US 7,224,472 B2
(45) Date of Patent: May 29, 2007

(54) OPERATION LAMP WITH CAMERA SYSTEM FOR 3D REFERENCING

(75) Inventors: Thomas Bauch, München (DE); Stefan Vilsmeier, Kufstein (AT)

(73) Assignee: BrainLAB AG, Feldkirchen (DE)

(*) Notice: Subject to any disclaimer, the term of this patent is extended or adjusted under 35 U.S.C. 154(b) by 712 days.

(21) Appl. No.: 10/134,976

(22) Filed: Apr. 29, 2002

(65) Prior Publication Data

US 2003/0164953 A1 Sep. 4, 2003

(30) Foreign Application Priority Data

Mar. 1, 2002 (EP) .................................. 02004345

(51) Int. Cl.
- G01B 11/24 (2006.01)
- G01B 11/30 (2006.01)
- G01B 11/14 (2006.01)
- A61B 1/06 (2006.01)
- A61B 5/05 (2006.01)

(52) U.S. Cl. .................. 356/611; 356/614; 356/620; 362/804; 600/249; 600/426

(58) Field of Classification Search ............... 356/611; 600/426–429
See application file for complete search history.

(56) References Cited

U.S. PATENT DOCUMENTS

| | | | | |
|---|---|---|---|---|
| 2,943,241 A | * | 6/1960 | Macnamara et al. | 315/316 |
| 5,603,328 A | * | 2/1997 | Zucker et al. | 600/479 |
| 5,745,545 A | * | 4/1998 | Hughes | 378/65 |
| 5,792,147 A | * | 8/1998 | Evans et al. | 606/130 |
| 5,803,905 A | * | 9/1998 | Allred et al. | 600/249 |
| 5,808,680 A | | 9/1998 | Steckhan | |
| 5,835,266 A | * | 11/1998 | Kitajima | 359/384 |
| 5,852,672 A | * | 12/1998 | Lu | 356/604 |
| 5,864,640 A | * | 1/1999 | Miramonti et al. | 382/312 |
| 5,924,976 A | * | 7/1999 | Stelzer et al. | 600/106 |
| 6,112,113 A | * | 8/2000 | Van Der Brug et al. | 600/427 |
| 6,151,521 A | * | 11/2000 | Guo et al. | 600/407 |

(Continued)

FOREIGN PATENT DOCUMENTS

| | | |
|---|---|---|
| EP | 0 421 130 | 4/1991 |
| EP | 0 793 945 | 9/1997 |
| WO | 99/27839 | 6/1999 |
| WO | 01/05161 | 1/2001 |

*Primary Examiner*—Gregory J. Toatley, Jr.
*Assistant Examiner*—Gordon J. Stock, Jr.
(74) *Attorney, Agent, or Firm*—Renner, Otto, Boisselle and Sklar, LLP

(57) ABSTRACT

The invention relates to a system for the combined shadow-free illumination of a pre-definable area and for referencing three-dimensional spatial co-ordinates, and to an active or passive referencing system, each in particular for referencing surgical or medical instruments. The system is characterized in that at least two cameras and the light source (operation lamp) are held together such that the optical signals detected by the cameras, for referencing three-dimensional spatial co-ordinates in the area illuminated by the light source, can be evaluated. Since the field of view of the light source, in its conventional use, is not obscured or only negligibly obscured, this field of view can simultaneously be used for optical navigation by the cameras held together with the light source. In accordance with the invention, the cameras are automatically aligned optimally for optical navigation.

The cameras can be rigidly or flexibly connected to the light source. The position and/or orientation of the cameras can be adjustable.

15 Claims, 4 Drawing Sheets

U.S. PATENT DOCUMENTS

| | | |
|---|---|---|
| 6,246,900 B1 | 6/2001 | Cundari et al. |
| 6,309,345 B1 | 10/2001 | Stelzer et al. |
| 6,328,458 B1 * | 12/2001 | Bell et al. .................. 362/371 |
| 6,359,647 B1 * | 3/2002 | Sengupta et al. ........... 348/154 |
| 6,405,072 B1 * | 6/2002 | Cosman ...................... 600/426 |
| 6,434,329 B1 * | 8/2002 | Dube et al. .................... 396/14 |
| 6,529,758 B2 * | 3/2003 | Shahidi ...................... 600/407 |
| 6,633,328 B1 * | 10/2003 | Byrd et al. .................. 348/143 |
| 6,873,867 B2 * | 3/2005 | Vilsmeier ................... 600/415 |
| 2002/0082498 A1 * | 6/2002 | Wendt et al. ............... 600/411 |

\* cited by examiner

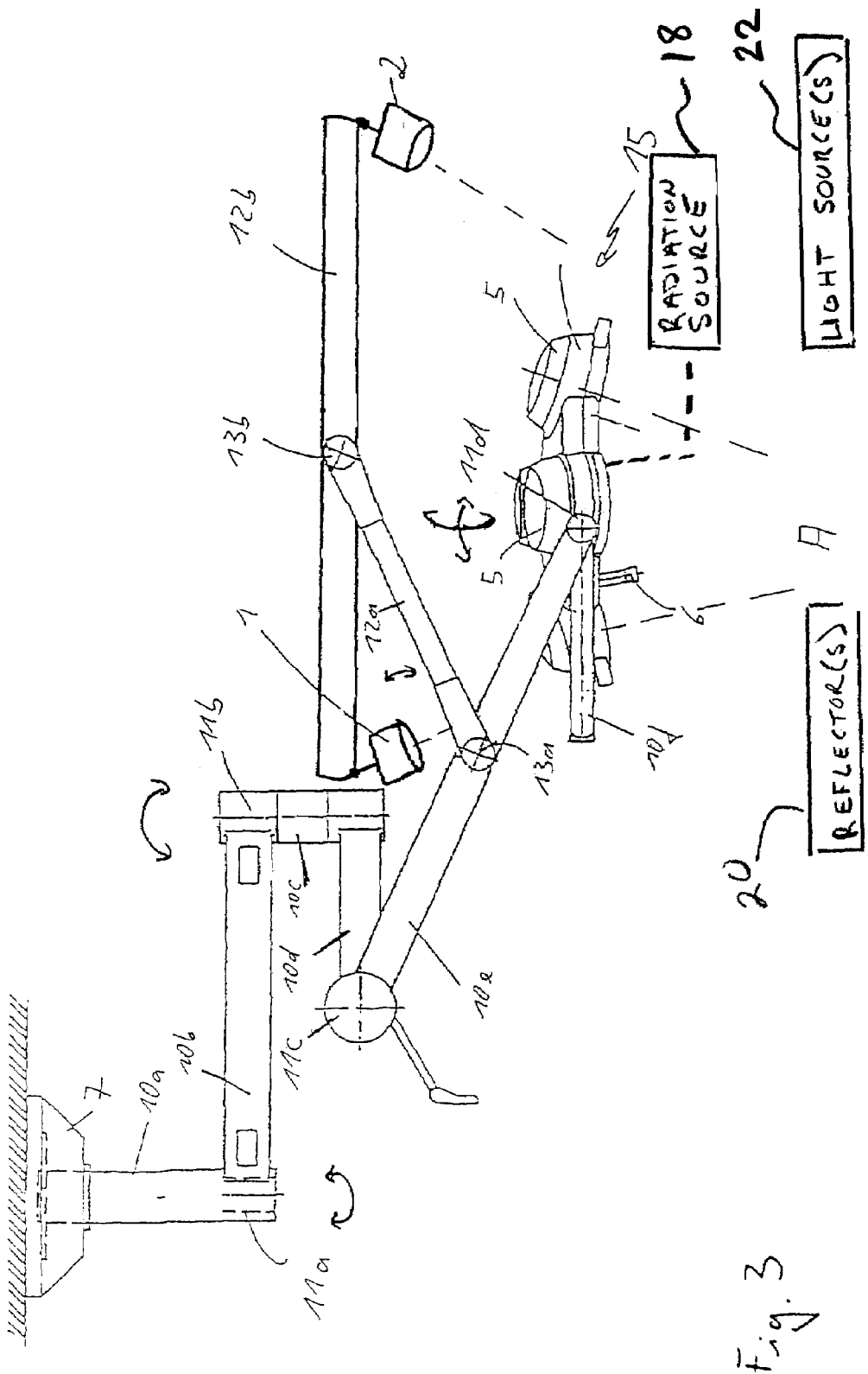

OPERATION LAMP WITH CAMERA SYSTEM FOR 3D REFERENCING

FIELD OF THE INVENTION

The present invention relates to a system for the combined, shadow-free illumination of a pre-definable area and for referencing three-dimensional spatial co-ordinates, in particular of surgical or medical instruments, and to a reflector referencing system.

BACKGROUND OF THE INVENTION

Referencing systems in the sense of this application are known for example from DE 196 39 615 C2, the content of the disclosure of which is explicitly incorporated by way of reference in the present application. Such systems, also known as navigation systems, provide the connection between the surgeon carrying out the treatment, i.e. the patient anatomy as the surgeon sees it during treatment, and diagnostic data obtained for example from computer tomography and represented visually by an image output via a computational unit. For detecting three-dimensional spatial co-ordinates, a plurality of markers with known dimensions are used, such as are for example described in DE 196 39 615 C2, line 2. A radiation source, in particular an infrared radiation source, illuminates the area in which three-dimensional spatial co-ordinates are to be detected, and the radiation reflected by the markers is detected with the aid of at least two cameras, each from a different angle of view. Alternatively, the objects to be referenced can also actively emit radiation, in particular infrared radiation, to which end radiation sources, for example LEDs, are attached to the objects, the radiation from which is detected as described above. The camera signals are evaluated with the aid of a subordinated computational unit and by means of known algorithms.

It is necessary for referencing for there to always be at least two cameras monitoring the area in which three-dimensional spatial co-ordinates are to be detected, from different angles of view, without the relevant field of view of the cameras being obscured. Here, it is desirable for the at least two cameras to be adjustable in the simplest way possible, in accordance with the respective circumstances.

To this end, DE 196 39 615 C2 discloses two cameras held by a common frame which have to be positioned laterally above the setting to be detected, for example the operating table. In certain situations, this can be difficult. In an operating theater, the suitable position for the cameras of the referencing system depends in particular on the positions at which the operating staff are standing around the operating table, and on where apparatus which could obscure the field of view of the cameras is positioned. It must be taken into account here that different operations may require different apparatus and positions. Suitably positioning and aligning the cameras is thus comparatively difficult.

In other referencing systems, the cameras are therefore either suspended from the ceiling of the operating theater or attached at other suitable points in the operating theater, for example to the computer itself or in the corners of the room. It can nonetheless easily transpire that the field of view of one or more may be obscured at the same time, making accurate referencing impossible. Positioning the cameras at a comparatively long distance from the relevant area in which three-dimensional spatial co-ordinates are to be detected also has the disadvantage that a comparatively large amount of zero order information is detected by the cameras, which can compromise the referencing accuracy, or at least unnecessarily increases the computational demands involved.

SUMMARY OF THE INVENTION

The present invention provides a system for referencing three-dimensional spatial co-ordinates, in particular of surgical or medical instruments, which is even easier to operate and adjust.

In accordance with a first aspect of the present invention, a combination is provided consisting of two individual systems known in their own right, namely a light source for the shadow-free illumination of an area of interest in which three-dimensional spatial co-ordinates are to be detected, and a camera system which is designed to reference three-dimensional spatial co-ordinates, in particular for referencing surgical and medical instruments, in a way known in its own right. In accordance with the invention, the light source and the camera system are combined with each other such that the light source and cameras are held together in such a way that the optical signals detected by the cameras for referencing three-dimensional spatial co-ordinates can be evaluated in an area which includes the area of shadow-free illumination by the light source or which is substantially identical to this.

The light source for the shadow-free illumination of an area is a light source used in operating theaters, but also in medical practices or dental surgeries. Such a light source may comprise one illuminating means or a plurality of illuminating means arranged point-symmetrically in the conventional way. Most particularly preferably, the camera system is combined in accordance with the invention with a conventional operation lamp. For pre-definable shadow-free illumination, such light sources are conventionally supported by a supporting arm construction comprising a number of joints, in order to be able to illuminate the area to be illuminated from above. By adjusting the supporting arm construction, the position and/or orientation of the light source with respect to the area to be illuminated can be changed in any way.

The present invention is based on the recognition that according to experience the light source is always positioned and/or orientated such that the area to be illuminated is optimally illuminated, which generally means that the line of sight from the light source to the area to be illuminated is not obstructed, be it by obstructive apparatus or by staff. The present invention then uses this substantially unobstructed line of sight in a surprisingly simple way and positions the cameras of the referencing system within or in the near vicinity of the light source as described in the following, such that the cameras which serve for referencing also have an unobstructed field of view onto the areas of interest. The present invention furthermore uses the fact that the relevant procedures for which three-dimensional spatial co-ordinates are to be detected are normally performed in the area of shadow-free illumination by the light source. Thus, in accordance with the invention, substantially unobscured, shadow-free illumination is combined in a surprisingly simple way with a substantially unobscured field of view of the referencing system camera.

In order to enable accurate referencing, the fields of view of the at least two cameras overlap, at least in the illuminated area. The area of overlap of the fields of view of the cameras can, however, also be larger than the illuminated area, which is particularly advantageous when the light source can be positioned and orientated independently of the referencing cameras. The at least two cameras thus monitor the illuminated area from at least two different angles of view, enabling three-dimensional spatial co-ordinates in the overlap area to be detected with the aid of known algorithms.

While the individual components, namely the light source and the camera system, known as such and in their own right from the prior art, are operated and installed independently in the prior art, the present invention is directed to a system comprising both individual components, in which the individual components are held together in such a way that both a shadow-free illumination of pre-definable areas and referencing three-dimensional spatial co-ordinates in the area illuminated in this way is possible. In principle, they can be held together such that both the cameras and the light source are suspended independently of each other from the ceiling, for example in an operating theater. In accordance with a preferred embodiment, however, at least two cameras of the referencing system and the light source are held together by means of a mechanical mounting. Most particularly preferably, the at least two cameras of the referencing system are held in the immediate vicinity of the light source, together with it. Since light sources for shadow-free illumination usually exhibit a circular or elliptical cross-section, the at least two cameras of the referencing system are arranged near the circumferential edge of the light source, and most particularly preferably, substantially in the plane spanned by the light source or protruding slightly from it. In principle, however, the cameras can also be arranged beyond the plane spanned by the light source.

In order to facilitate referencing, the at least two cameras are arranged in the immediate vicinity of the light source in such a way that the field of view of each of the cameras is not obscured by the light source or by the casing of the light source. Since the fields of view of the cameras are supposed to overlap in the illuminated area, the cameras are usually inclined relative to the optical axis of the light source. Thus, if the cameras are arranged beyond the plane spanned by the light source, then the cameras inclined radially inwards are offset radially outwards, such that the field of view of the cameras is not obscured by the circumferential edge of the light source.

In accordance with a particularly preferred embodiment, at least two cameras are integrated in the casing of the light source and aligned substantially parallel to the optical axis of the light source. This embodiment is based on the recognition that a surgeon or physician carrying out the treatment does not generally bend so far forward that the light source is obscured, rather the surgeon or physician usually only works with his hands and medical apparatus in the illuminated area. Advantageously, the referencing cameras are optimally orientated automatically because the area to be referenced usually has to be optimally illuminated.

The cameras integrated in the light source are preferably arranged in sections of the light source where no illuminating means are provided. Conventionally, operating lamps have a number of illuminating means, which are typically arranged point-symmetrically around the center of the light source. In this way, for example, a number of emitters arranged point-symmetrically can be integrated in a substantially round lamp casing. Openings are situated on the base of the lamp casing which can also be covered by glass windows through which light is emitted onto the operating table. There are therefore also unbroken areas on the base of the lamp casing which may be used for the referencing cameras. Preferably, viewing windows are provided in each of these areas for the referencing cameras, which can likewise be covered by a glass window or the like, so as not to change the convection ratios in the operation lamp. In this embodiment, the cameras can be aligned substantially parallel to the optical axis of the light source, since the distance between the referencing cameras can be selected to be comparatively small. The integrated design enables the cameras to be optimally orientated in a particularly simple way. At the same time, it is ensured that wherever the operation lamp is employed, referencing cameras are always also available. An operation can therefore be started more quickly, which in the case of mobile operation lamps in particular is of particular advantage. At the same time, the referencing cameras are protected by the casing of the light source.

In the above embodiment, further cameras can of course also be arranged outside the casing of the light source, for example in the manner described above. These are preferably held together with the lamp casing or are attached, for example, to its circumferential edge. The pairs of cameras can be arranged aligned on a common axis or on intersecting axes, for example mutually orthogonal axes.

In accordance with a preferred embodiment, the referencing cameras are rigidly connected to the light source. When the position and/or the orientation of the cameras has been correctly set once, the cameras do not require further adjustment. This thus optimally ensures that the cameras are always correctly positioned and orientated.

In accordance with a further embodiment, however, the orientation and/or positioning of one or of at least two cameras can be adjusted relative to the light source, enabling them to be even more flexibly adjusted to the respective circumstances, for example when using particularly high or bulky apparatus in an operating theater, when there are particularly tall people standing around the operating table, and the like.

In principle, any arrangements can be predefined for the referencing cameras relative to the light source. In accordance with a preferred embodiment, however, the cameras are arranged substantially point-symmetrically to the center of the light source. Most particularly preferably, two cameras are respectively arranged on opposite sides of the light source. If more than three cameras are provided, then these can for example be arranged point-symmetrically with respect to the center of the light source.

In accordance with a further embodiment, a number of cameras, for example two cameras, are respectively combined into groups of cameras, wherein the cameras of a group may be jointly adjusted by means of adjusting elements, in order to adopt a new position and/or orientation relative to the light source. The groups can be arranged aligned on a common axis or on intersecting axes, for example mutually orthogonal axes.

To this end, the cameras of a camera group can be attached to a common mechanical adjusting group. In accordance with a preferred embodiment, the inclination angles by which the cameras are inclined relative to the optical axis of the light source, are adjusted together, the cameras preferably being inclined symmetrically relative to the optical axis of the light source. If, for example, two cameras of the camera group are arranged on opposite sides of a substantially round light source, then the inclination angles of the cameras are preferably adjusted in the opposite direction with respect to the center of the light source, such that in a particularly advantageously simple way, the area of overlap of the cameras can be adjusted, the focus of the area of overlap always corresponding to the focus of the area illuminated by the light source.

The above joint mobility of the light source and cameras does not exclude the light source from also being movable completely independently of the cameras for particular purposes, for example if an area is to be illuminated laterally or if a further light source is to be connected up as well. The person skilled in the art will easily recognize suitable mechanical mountings while studying the following description of the preferred embodiments.

Cameras are conventionally used for referencing which only detect optical signals in the infrared spectral range. Such signals can be generated by one or more radiation sources (e.g., a grouo of radiation sources). To this end, the visible spectrum is usually blocked off with the aid of infrared transmission filters. The infrared transmission filters allow infrared radiation reflected by a reflector (or group of reflectors) or emitted by a light source (or group of light sources) to be detected buy one or more cameras, while inhibiting light in the visible spectrum. Since on the one hand, high optical power output is desired of the light source, especially in operating theaters, but on the other hand, an excessive heat load in the illuminated area is to be avoided, then in accordance with a particularly preferable embodiment, the infrared portion of the radiation from the light source is filtered out, at least partly, with the aid of filters. In this way, disruptive impairing of the optical signals detected by the cameras can be avoided. Measures for filtering the light from the light source are known to the person skilled in the art of operation lamps.

Most particularly preferably, the system in accordance with the invention comprises at least three cameras for referencing. If the field of view of one camera is obscured, for example by apparatus or people, then the system can shift to another camera, whose field of view is not obscured, to detect optical signals. In order that this change to another camera is automatic, an evaluation circuit is provided in accordance with said preferred embodiment, which evaluates the electronic signals detected by the cameras. When the field of view of the camera is obscured, this is often marked by characteristic signals, on the basis of which the evaluation circuit analyses the signals detected. An obscured area can, for example, make itself noticeable by a sudden change in intensity in the area detected. If such characteristic signals are established, then the evaluation circuit no longer transmits the electrical signals of the obscured signals to the computer used for referencing, but instead automatically changes to another camera for which no obscuring is detected based on the characteristic signals.

A second aspect of the present invention is directed to a referencing system such as is known for example from DE 196 39 615 C2. In accordance with the invention, this system is marked by the at least two cameras and the light source for the shadow-free illumination of an area being held together such that the signals for referencing three-dimensional spatial co-ordinates in the illuminated area may be evaluated. To this end, the camera system and the light source are designed in accordance with the embodiments described above in connection with the first aspect. The referencing system can work actively or passively, in the sense that the light is either emitted from light sources attached to the objects to be referenced, or reflected by reflectors attached to the objects to be referenced.

Preferred embodiments of the present invention will now be described by way of example and with reference to the attached drawings, in which:

BRIEF DESCRIPTION OF THE DRAWINGS

FIG. 3 shows a side view of a second embodiment of the system in accordance with the present invention.

DETAILED DESCRIPTION

In the figures, identical reference numbers indicate identical or similarly effective elements or components.

Figure 1A:
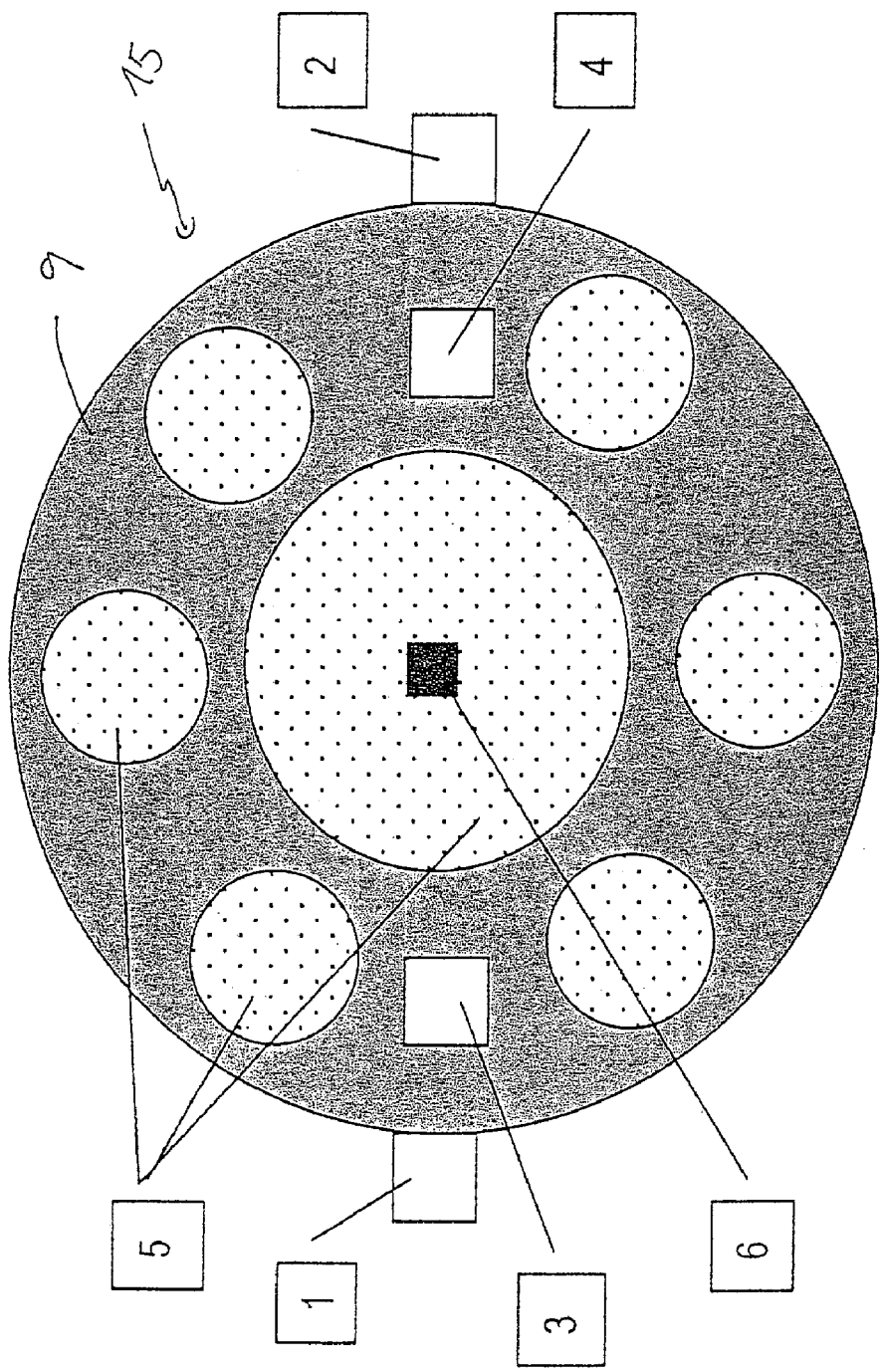
FIG. 1a/1b is a schematic underside view of a system in accordance with a first embodiment of the present invention, and a modification thereof.
Figure 1B:
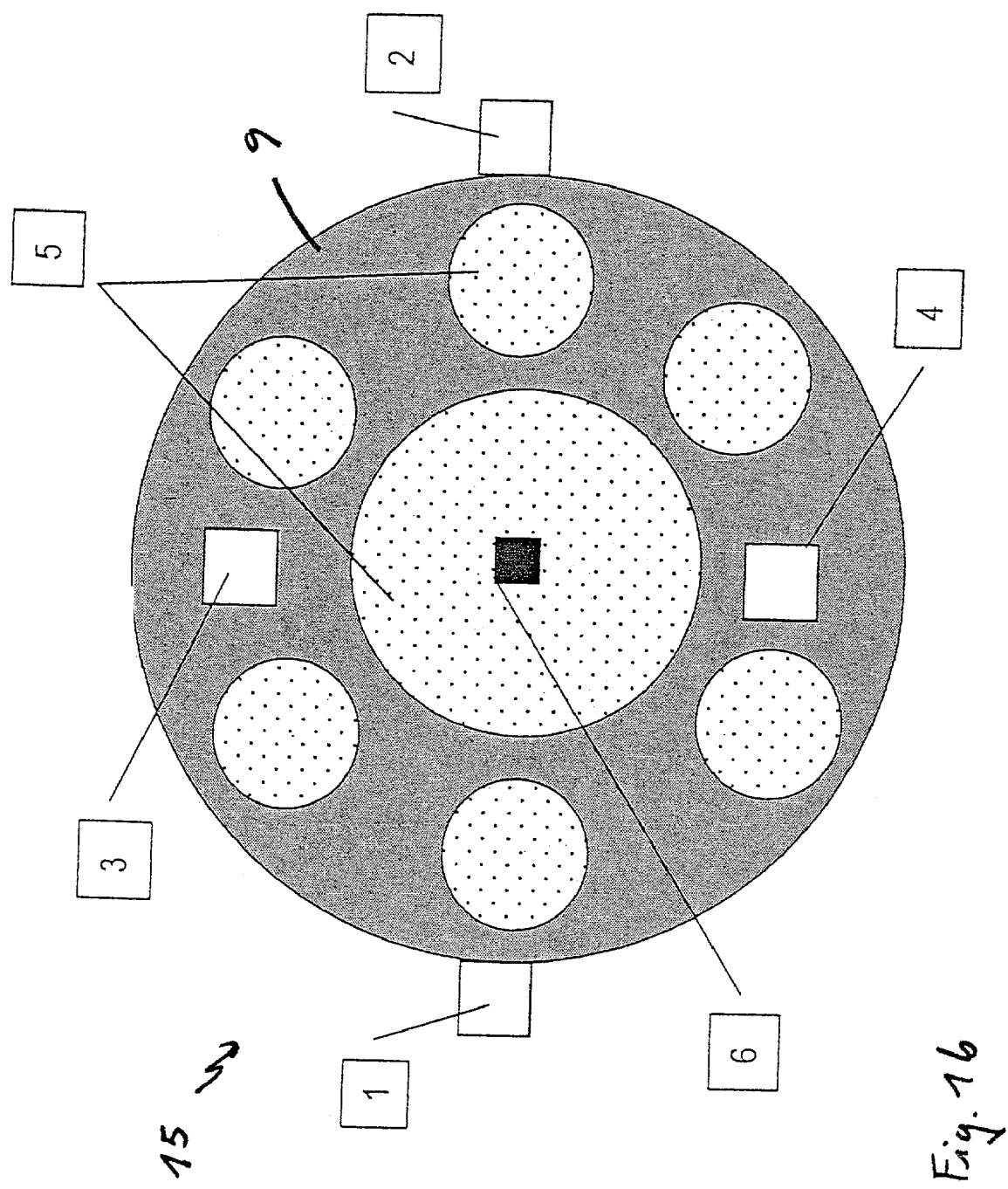
Figure 2:
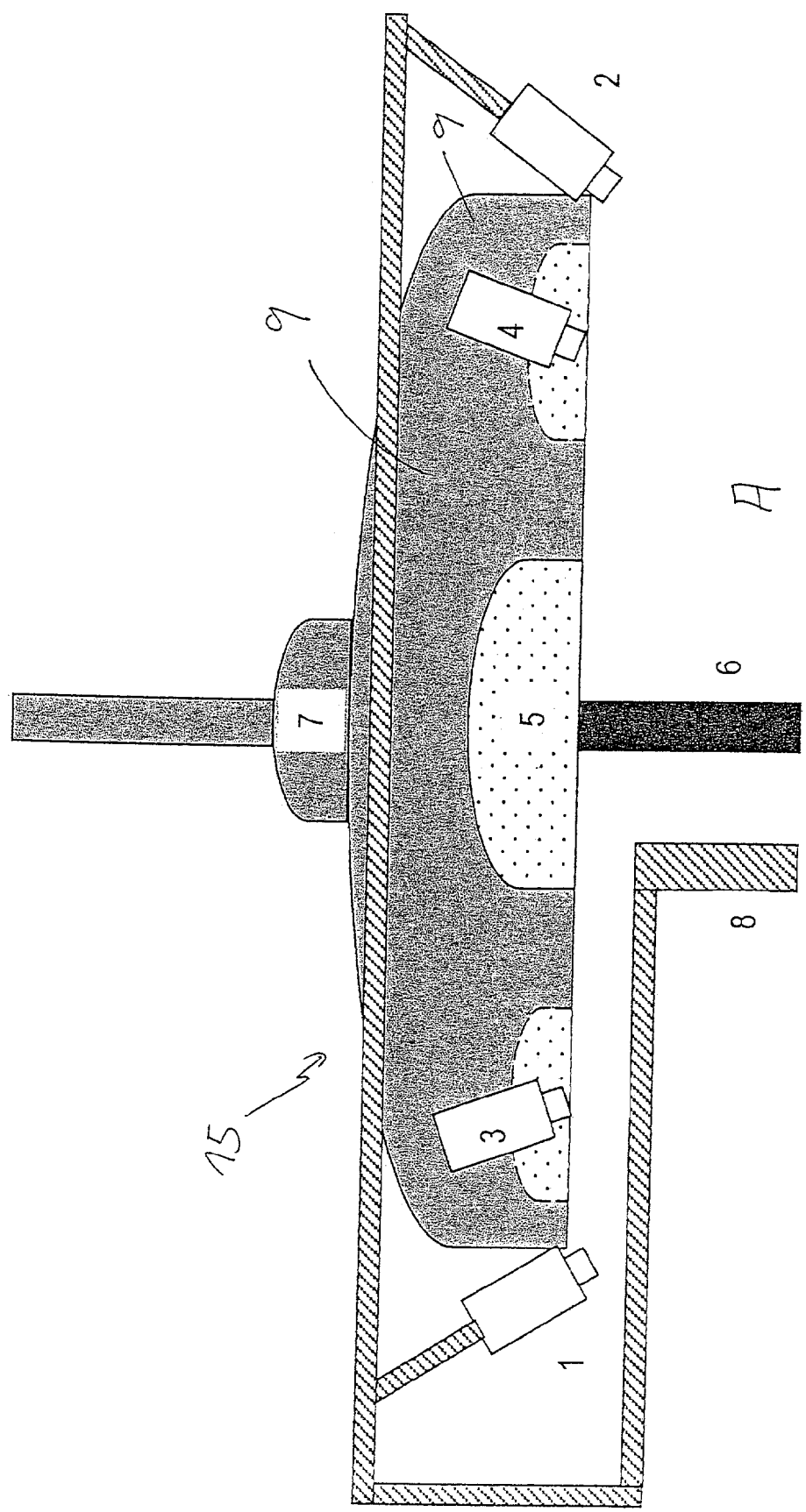
FIG. 2 is a cross-section through the first embodiment in accordance with FIG. 1.

FIGS. 1 and 2 show a schematic underside view and a cross-section of a system in accordance with a first embodiment of the present invention. The system comprises the light source 15 and four cameras 1 to 4, which serve to reference three-dimensional spatial co-ordinates in accordance with the optical navigation method described in DE 196 39 615 C2. To this end, the signals detected by the cameras 1 to 4 are transmitted to a subordinated computational unit (not shown). The light source 15 has a circular cross-section and comprises a central illuminating means 5 and six illuminating means 5 arranged point-symmetrically to it, each held in the casing 9. The illuminating means 5 provide an area A with substantially shadow-free illumination. To this end, the illuminating means 5 can emit the light substantially vertically from the plane spanned by the base of the casing 9, or they can be inclined at an angle, as is known to the person skilled in the art in this field. Conventionally, the light source 15 is held above the illuminated area A, to which end a ceiling mounting (not shown) or the like is provided, such as is shown by way of example in FIG. 3. With the aid of the centrally or laterally arranged handle 6, the light source 15 can be positioned and/or orientated in any way relative to an object. Shifting is counteracted by sufficient forces, such that the position, once adopted, does not change again by itself.

For operation purposes, the light source 15 conventionally exhibits a comparatively large diameter, for example in the range 60 to 80 cm. The luminosity and orientation of the illuminating means are preferably selected such that a conventional working distance is ensured for optimum illumination of an area, for example a distance of about 107 cm or in the range between about 91 and 123 cm between the light source and the working area to be illuminated.

The infrared portion of the light emitted by the illuminating means 15 can at least in part be filtered out, to which end the openings in the base of the lamp casing 9 visible in FIG. 1 are provided with suitable optical elements, for example dichroitic reflectors, which using a heat absorber (not shown) reflect the infrared spectral portion according to wave length, while the visible spectral portion is allowed through the openings in the lamp casing 9. The openings can of course be covered with cover windows. Additional convection openings (not shown) can also be provided in the base of the lamp casing 9, such that a stream of air passing through the lamp prevents the components in the lamp interior from overheating.

Three cameras 1, 2 are arranged in the immediate vicinity of the circumferential edge of the light source 15, said cameras being inclined inwards relative to the optical axis of the light source 15 running through the handle 6, as shown in FIG. 2. The cameras 1, 2 can be directly mounted on the external circumferential edge of the lamp casing 9, or on a common arm attached either to the lamp casing 9 itself or in the immediate vicinity of the lamp casing 9. To this end, the holding arm (not shown) can also be suspended from the ceiling. As can be seen in FIG. 2, the field of view of the cameras 1, 2 is not obstructed by sections of the lamp casing 9. The fields of view of the cameras 1, 2 overlap in the area A, enabling stereoscopic spatial detection and therefore enabling three-dimensional spatial co-ordinates to be detected at least in the area A. The longitudinal axes of cameras 1,2 are substantially aligned with the optical axis of the light source 15. This means that the plane spanned by the longitudinal axes of the cameras 1, 2 incorporates the optical axis of the light source 15 running substantially through the handle 6, or is arranged in its vicinity.

Two further cameras 3, 4 are integrated in the lamp interior which monitor the area A through recesses in the base of the lamp casing 9. Viewing windows and/or infrared filters can be attached in the recesses. As can be seen in FIG. 2, the cameras 3, 4 are also inclined relative to the optical axis of the light source 15 and overlap at least in the area A in order to enable stereoscopic detection there and therefore enabling three-dimensional spatial co-ordinates to be referenced.

Due to the cameras 1 to 4 being held together with the light source 15, the cameras are automatically orientated such that the area A illuminated by the light source 15 can also be referenced.

The cameras 1, 2 arranged on the external circumferential edge of the lamp casing 9 can of course also be arranged above the light source. In order that the fields of view of these cameras are not obstructed by the lamp casing 9, the cameras 1, 2 are arranged offset radially outwards, outside a truncated cone the delimiting surfaces of which are substantially pre-defined by the longitudinal axes of the cameras 1, 2 shown in FIG. 2.

In principle, at least the cameras 1, 2 can also be positioned and/or orientated independently of the light source 15. To this end, the additional handle 8 shown schematically in FIG. 2 is provided, which in principle can also be integrated in the handle 6. By adjusting the handle 8, suitable positioning and orientation movements of at least the cameras 1, 2 and possibly also of the cameras 3, 4 are triggered. The inclination angle of the cameras, for example, can be changed relative to the optical axis of the light source 15, the inclination angle of the cameras can be changed perpendicular to the drawing plane in FIG. 2, and the radial position of the cameras can be varied. The adjustments can be made manually with the aid of the handgrip 8. One or more motorized adjusting elements can of course also be provided, for example electrical adjusting motors operable individually or in groups by the handle 8. The adjusting motors can be provided with control commands by a wire connection or wirelessly.

The person skilled in the art in this field will easily recognize suitable mountings for the cameras while studying this patent description. Adjustment is directed to requirements, and may comprise axial shifting and/or rotation about the longitudinal axis of the cameras and/or pivoting about the longitudinal axis of the cameras in one or two spatial directions, etc.

While in FIG. 1a, the two groups of cameras 1, 2 and 3, 4 are arranged aligned on a common axis, in FIG. 1b the two groups of cameras are arranged on mutually orthogonal axes which intersect at the center of the light source.

FIG. 3 shows a schematic side view of a second embodiment of the system in accordance with the invention. This system comprises the light source 15 and the cameras 1, 2 which are suspended together from the ceiling by a supporting arm construction. The supporting arm construction comprises a number of arms 10a–f extending from the ceiling attachment 7 and which can be axially rotated at the joints 11a, 11b and pivoted perpendicular to the second plane in FIG. 3 in the joint areas 11c and 11b, such that within the range of the arms 10a–f, the light source 15 can be positioned and orientated in almost any way with respect to an object which is to be illuminated. The light source 15 itself comprises three illuminating means 5 which illuminate the area A in star-shaped, point-symmetrical arrangement. The cameras 1, 2 are held by the common arm 12a, 12b of the camera suspension 12a, 12b. The arms 12a, 12b can be pivoted about the joints 13a, 13b, perpendicular to the drawing plane in FIG. 3, as shown. Instead of the pivoting mounting, a camera suspension which is fixed relative to the light source 15 can of course also be provided. The distance of the arm 12b relative to the light source 15 is preferably small, for example in the range 5 to 50 cm, preferably in the range of about 5 to about 30 cm, and even more preferably in the range of about 5 to about 15 cm.

As shown in FIG. 3, the cameras 1, 2 are inclined radially inwards such that their fields of view overlap at least in the illuminated area A, in order to enable 3D referencing. Also shown in FIG. 3 is a radiation source 18 attached to the light source 15. The radiation source 18 emits, for example, infrared light. Further, a plurality or group of reflectors 20, and a plurality or group of light sources 22 also are shown. The reflectors 20 reflect optical radiation generated by the radiation source 18, while the light sources 22 generate optical radiation (e.g. infrared LEDs).

By pivoting the arms 12a, 12b of the camera suspension and/or adjusting the adjusting motors (not shown), the field of view of the cameras 1, 2 can be suitably changed.

A detection means can be provided in the light source 15, said means deducing the position of the illuminated area A from the orientation of the light source 15. A detection means can in turn be provided on the camera suspension 12a, 12b, said means automatically detecting the positional relationship of the cameras 1, 2 with respect to the light source 15 and therefore with respect to the illuminated area A. When the light source 15 is adjusted, and the illuminated area A therefore changed, a computational unit (not shown) calculates whether the area detected by the cameras 1, 2 in which referencing is possible (the above-mentioned area of overlap), also comprises the currently illuminated area A. If this is not the case, then a control signal is calculated which can be used to adjust the cameras 1, 2 using motors.

As shown in FIG. 3, the cameras 1, 2 are orientated such that their fields of view are not obstructed or only negligibly obstructed by the light source 15. In principle, the cameras 1, 2 can also be automatically adjusted using motors in the way described above, if the field of view of the cameras is obscured by the light source 15. In this respect, information regarding the external dimensions of the light source must be available to the above-mentioned computational means.

The cameras are conventionally CCD video cameras, such that the detected optical signals are provided in digital form for evaluation. On the basis of characteristic changes in signal, for example sudden changes in intensity, it is thus possible to immediately establish if the field of view of a camera has suddenly been obstructed. In order to always ensure suitable referencing, an evaluation circuit (not shown) is provided which examines the respective electrical signals from the cameras 1–4. If a characteristic change in signal is detected which indicates an obstruction of the field of view of the camera, then the evaluation circuit automatically changes to one of the other cameras 1–4 and transmits the signal from this camera to the computational unit of the referencing system. In a predefined scheme, the electronic signals from the cameras 1–4 can also be periodically checked by the computational unit as to whether the respective field of view has just been obstructed. Then, according to a pre-defined algorithm, the computational unit can establish which of the cameras 1–4 should be used for referencing. On the basis of the common mounting of the camera system and the light source, the connections necessary to operate the light source 15 and the video cameras 1–4 can be led through from the ceiling attachment 7 as a common connecting cable.

In principle, the individual components for the system claimed can also be operated individually. In accordance with a preferred embodiment, the system in accordance with the invention is characterized in particular by the light source and the video cameras being held together, such that three-dimensional spatial co-ordinates can be referenced in the area currently being illuminated by the light source 15. To this end, the cameras are in particular arranged in the immediate vicinity of the light source 15.

The invention claimed is:

1. A system for the combined illumination of a medical workspace and referencing of three-dimensional spatial coordinates of surgical or medical instruments, comprising:
   - an operation lamp producing shadow-free illumination in the visible spectrum for the shadow-free illumination of said medical workspace; and
   - at least two cameras for detecting optical signals, wherein said operation lamp and said at least two cameras are mounted with respect to one another such that when the operation lamp is moved the cameras are correspondingly moved to retain the same positional relationship, for referencing three-dimensional spatial coordinates in said illuminated medical workspace.

2. The system as set forth in claim 1, wherein the orientation and/or position of the at least two cameras may be adjusted relative to said operation lamp.

3. The system as set forth in claim 1, wherein the at least two cameras are arranged substantially point-symmetrically with respect to said center of said operation lamp.

4. The system of claim 1, further comprising a radiation source for emitting infrared radiation, and the at least two cameras detect the infrared radiation.

5. A system for the combined illumination of a medical workspace and referencing of three-dimensional spatial coordinates of surgical or medical instruments, comprising:
   - an operation lamp producing shadow-free illumination in the visible spectrum for the shadow-free illumination of said medical workspace; and
   - at least two cameras for detecting optical signals, wherein said operation lamp and said at least two cameras are mounted together for common movement such that said optical signals may be evaluated, for referencing three-dimensional spatial coordinates in said illuminated medical workspace, wherein the at least two cameras are arranged outside a casing of the operation lamp and near a circumferential edge of said casing, such that the sight of said at least two cameras onto said illuminated area is not obstructed by sections of said casing.

6. The system as set forth in claim 5, wherein the at least two cameras are integrated in said casing of said operation lamp, viewing windows being respectively provided for said at least two cameras on sections of said casing where no illuminating means of said operation lamp are arranged.

7. The system as set forth in claim 5, wherein the at least two cameras are external to said casing of said operation lamp.

8. A system for the combined illumination of a medical workspace and referencing of three-dimensional spatial coordinates of surgical or medical instruments, comprising:
   - an operation lamp producing shadow-free illumination in the visible spectrum for the shadow-free illumination of said medical workspace; and
   - at least two cameras for detecting optical signals, wherein said operation lamp and said at least two cameras are held together such that said optical signals may be evaluated, for referencing three-dimensional spatial coordinates in said illuminated medical workspace, wherein said operation lamp and the at least two cameras are rigidly connected to each other such that said operation lamp and said cameras may be moved together.

9. A system for the combined, shadow-free illumination of a medical workspace and referencing of three-dimensional spatial coordinates of surgical or medical instruments, comprising:
   - an operation lamp producing shadow-free illumination in the visible spectrum for the shadow-free illumination of said medical workspace; and
   - at least two cameras operable to detect non-visible light signals, wherein the orientation and/or position of at least two cameras may be adjusted relative to said operation lamp, wherein the at least two cameras arranged respectively on opposite sides of said operation lamp may be moved together, an inclination angle of said at least two cameras being adjustable, in the opposite direction, with respect to the center of said operation lamp.

10. A system for the combined illumination of an area and referencing of three-dimensional spatial coordinates of surgical or medical instruments, comprising:
    - an operating light source producing light in the visible spectrum for illumination of said area; and
    - at least two cameras for detecting optical signals, wherein said operating light source and said at least two cameras are held together such that movement of the operating light source produces a corresponding movement in the at least two cameras to enable evaluation of said optical signals, for referencing three-dimensional spatial coordinates in said illuminated area, wherein said at least two cameras are provided with infrared transmission filters in order to detect infrared radiation reflected by reflectors or emitted by light sources, the infrared portion of said light emitted from said operating light source being at least in part filtered out.

11. A system for the combined, shadow-free illumination of an area and referencing of three-dimensional spatial coordinates of surgical or medical instruments, comprising:
    - an operation lamp for the shadow-free illumination of said area; and
    - at least three cameras operative to detect non-visible light signals, wherein an evaluation circuit is provided to evaluate the signals detected by said at least three cameras, in order to detect when the field of view of at least one camera is obstructed, and in order—for referencing—to change from said respective camera with the obstructed field of view to another camera of said at least three cameras, whose field of view is not obstructed.

12. A reflector referencing system for surgical or medical instruments and for apparatus for treatment, comprising:

at least two cameras;

a computational unit connected to said at least two cameras, for evaluating camera signals and for referencing three-dimensional spatial coordinates;

a radiation source for infrared radiation; and a group of reflectors comprising at least two reflectors for said infrared radiation;

wherein said at least two cameras detect said infrared radiation reflected by said group of reflectors, wherein said at least two cameras and an operating light source producing light in the visible spectrum for the illumination of an area are mounted with respect to one another such that when the operating light source is moved the at least two cameras are correspondingly moved to retain the same positional relationship, for referencing three-dimensional spatial coordinates in said illuminated area.

13. A referencing system for surgical or medical nstruments and for apparatus for treatment, comprising:

at least two cameras;

a computational unit connected to said cameras, for evaluating camera signals and for referencing three-dimensional spatial coordinates;

a group of radiation sources comprising at least two radiation sources for producing infrared radiation; wherein said at least two cameras detect said infrared radiation emitted by said group of radiation sources; and wherein said at least two cameras and an operating light source producing light in the visible spectrum for the illumination of an area are mounted with respect to one another such that when the light source is moved the at least two cameras are correspondingly moved to retain the same positional relationship, for referencing three-dimensional spatial coordinates in said illuminated area.

14. A system for the combined illumination of a medical workspace and referencing of three-dimensional spatial coordinates of surgical or medical instruments, comprising:

an operation lamp producing shadow-free illumination in the visible spectrum for the shadow-free illumination of said medical workspace;

a radiation source for emitting infrared radiation; and at least two cameras for detecting optical infrared signals, wherein said operation lamp and said at least two cameras are held together such that movement of the operating lamp produces a corresponding movement in the at least two cameras to enable evaluation of said infrared signals, for referencing three-dimensional spatial coordinates in said illuminated medical workspace.

15. A method for positioning at least two cameras so as to monitor a medical workspace, said at least two cameras being operable to detect non-visible light, comprising:

moving an operation lamp so as to provide shadow free illumination of the medical work space; and automatically moving the at least two cameras to correspond to the movement of the operation lamp.

* * * * *